US008127396B2

(12) United States Patent
Mangiardi

(10) Patent No.: US 8,127,396 B2
(45) Date of Patent: Mar. 6, 2012

(54) ROBOTIC FLOOR CLEANING WITH STERILE, DISPOSABLE CARTRIDGES

(75) Inventor: John R. Mangiardi, Greenwich, CT (US)

(73) Assignee: Optimus Services AG, Maur (CH)

( * ) Notice: Subject to any disclaimer, the term of this patent is extended or adjusted under 35 U.S.C. 154(b) by 460 days.

(21) Appl. No.: 11/996,013

(22) PCT Filed: Jul. 20, 2006

(86) PCT No.: PCT/US2006/028228
§ 371 (c)(1),
(2), (4) Date: Feb. 6, 2008

(87) PCT Pub. No.: WO2007/037792
PCT Pub. Date: Apr. 5, 2007

(65) Prior Publication Data
US 2008/0209665 A1    Sep. 4, 2008

Related U.S. Application Data

(60) Provisional application No. 60/701,106, filed on Jul. 20, 2005.

(51) Int. Cl.
*A47L 5/00* (2006.01)
*A47L 11/00* (2006.01)
*G06F 19/00* (2006.01)

(52) U.S. Cl. .............. 15/319; 15/320; 15/339; 15/340.3

(58) Field of Classification Search .............. 15/319, 15/320, 339, 340.3; *A47L 5/00, 11/00; G06F 19/00*
See application file for complete search history.

(56) References Cited

U.S. PATENT DOCUMENTS 5,279,672 A    1/1994    Betker
(Continued)

FOREIGN PATENT DOCUMENTS

FR    2857843    1/2005
(Continued)

OTHER PUBLICATIONS

EP Search Report for Ser. No. 06 83 6089, dated Mar. 5, 2010.
(Continued)

*Primary Examiner* — David Redding
(74) *Attorney, Agent, or Firm* — Buckley, Maschoff & Talwalkar LLC

(57) ABSTRACT

An automated (robotic) floor cleaner (100) is adapted to allow sterile cleaning of sensitive environments, such as hospital room. In particular, the floor-cleaner chassis (124) is redesigned to be mounted on a deck (102) containing cleaning devices that contact the floor. The cleaning devices mounted on the deck (102) include vacuum head (132), brushes (120), cleaning fluid sprays (128), and conceivably sanitizing devices such as UV germicidal light, are provided pre-sterilized. As such, the adapted floor-cleaner chassis (124) allows the deck (102) to be mounted to the bottom of the chassis (124), the floor-cleaner (100) is then used to clean a floor, after which, the deck (102) is removed from the chassis (124) and disposed. The robotic-floor cleaner (100) and sterilization system cleans floor between or even during cases. Further, the robotic floor cleaner (100) reduces the "turnover time" required between cases, as it operates simultaneously while the staff prepares the room for the next case.

12 Claims, 2 Drawing Sheets

U.S. PATENT DOCUMENTS

| | | | |
|---|---|---|---|
| 5,709,007 A | 1/1998 | Chiang |
| 5,714,119 A | 2/1998 | Kawagoe |
| 5,781,960 A | 7/1998 | Kilstrom et al. |
| 5,959,423 A | 9/1999 | Nakanishi |
| 6,263,989 B1 | 7/2001 | Won |
| 6,431,296 B1 | 8/2002 | Won |
| 6,535,793 B2 | 3/2003 | Allard |
| 6,594,844 B2 | 7/2003 | Jones |
| 6,605,156 B1 | 8/2003 | Clark et al. |
| 6,615,885 B1 | 9/2003 | Ohm |
| 6,661,239 B1 | 12/2003 | Ozick |
| 6,662,889 B2 | 12/2003 | De Fazio |
| 6,668,951 B2 | 12/2003 | Won |
| 6,690,134 B1 | 2/2004 | Jones |
| 6,769,004 B2 | 7/2004 | Barrett |
| 6,781,338 B2 | 8/2004 | Jones |
| 6,809,490 B2 | 10/2004 | Jones |
| 6,845,297 B2 | 1/2005 | Allard |
| 6,860,206 B1 | 3/2005 | Rudakevych |
| 6,870,792 B2 | 3/2005 | Chiappetta |
| 6,883,201 B2 | 4/2005 | Jones et al. |
| 6,940,291 B1 | 9/2005 | Ozick |
| 6,956,348 B2 | 10/2005 | Landry |
| 6,965,209 B2 | 11/2005 | Jones |
| 6,967,275 B2 | 11/2005 | Ozick |
| 7,024,278 B2 | 4/2006 | Chiappetta |
| 7,117,067 B2 | 10/2006 | McLurkin |
| 7,143,696 B2 | 12/2006 | Rudakevych |
| 7,155,308 B2 | 12/2006 | Jones |
| 7,173,391 B2 | 2/2007 | Jones |
| 7,188,000 B2 | 3/2007 | Chiappetta |
| 7,196,487 B2 | 3/2007 | Jones |
| 7,254,464 B1 | 8/2007 | McLurkin |
| 7,331,436 B1 | 2/2008 | Pack |
| 7,332,890 B2 | 2/2008 | Cohen |
| 7,363,994 B1 | 4/2008 | DeFazio |
| 7,369,460 B2 | 5/2008 | Chiappetta |
| 7,389,156 B2 | 6/2008 | Ziegler |
| 7,499,774 B2 | 3/2009 | Barrett |
| 7,499,775 B2 | 3/2009 | Filippov |
| 7,499,776 B2 | 3/2009 | Allard |
| 7,499,804 B2 | 3/2009 | Svendsen |
| 7,559,269 B2 | 7/2009 | Rudakevych |
| 7,571,511 B2 | 8/2009 | Jones |
| 7,597,162 B2 | 10/2009 | Won |
| 7,620,476 B2 | 11/2009 | Morse |
| 7,706,917 B1 | 4/2010 | Chiappetta |
| 2001/0037163 A1 | 11/2001 | Allard |
| 2002/0189871 A1 | 12/2002 | Won |
| 2004/0187249 A1 | 9/2004 | Jones |
| 2005/0022844 A1 | 2/2005 | Field |
| 2005/0055792 A1 | 3/2005 | Kisela |
| 2005/0156562 A1 | 7/2005 | Cohen |
| 2005/0251292 A1 | 11/2005 | Casey |
| 2006/0136096 A1 | 6/2006 | Chiappetta |
| 2006/0190133 A1 | 8/2006 | Konandreas |
| 2006/0190134 A1 | 8/2006 | Ziegler |
| 2006/0190146 A1 | 8/2006 | Morse |

FOREIGN PATENT DOCUMENTS

| | | |
|---|---|---|
| FR | 2857845 | 1/2005 |
| JP | 2003180587 | 7/2003 |
| JP | 2003180587 A | 7/2003 |
| WO | WO 2004/043215 A1 | 5/2004 |

OTHER PUBLICATIONS

International Preliminary Report on Patentability dated Jan. 22, 2008 for Ser. No. PCT/US2006/028228.

RU Official Action for Ser. No. 2008106443, dated Jun. 22, 2010.

Written Opinion of the ISA dated Jan. 22, 2008 for Ser. No. PCT/US2006/028228.

ROBOTIC FLOOR CLEANING WITH STERILE, DISPOSABLE CARTRIDGES

CROSS-REFERENCE TO RELATED APPLICATIONS

This application is a national stage of application serial no. PCT/US06/28228, filed Jul. 20, 2006, which claims the benefit under 35 U.S.C. §119(e) of U.S. Provisional Application No. 60/701,106, filed Jul. 20, 2005, the contents of all of which are incorporated herein in their entireties by reference thereto.

The following references are hereby explicitly incorporated by reference thereto:
- U.S. Pat. No. 6,605,156 B1
- U.S. Pat. No. 6,883,201
- Applications filed along with present application by current inventor on this date entitled:
  - IN-CEILING FOCUS LOCATED SURGICAL LIGHTING
  - HOSPITAL OPERATING ROOM RE-DESIGN
  - AMBIENT LIGHTING IN HOSPITAL SURGICAL ENVIRONMENTS
  - USE OF ULTRAVIOLET GERMICIDAL IRRADIATION IN HEALTH CARE ENVIRONMENTS
  - IN-WALL WASTE RECEPTACLES FOR HOSPITAL AND LABORATORY ENVIRONMENTS
  - MULTIFUNCTIONAL FLOOR PODS
  - RE-DESIGN OF OPERATING ROOM TABLES

BACKGROUND OF THE INVENTION

1. Field of Invention

The present invention relates to a disposable, sterile cartridge for use with a robotic floor-cleaning device and a method of using said disposable, sterile cartridge and said robotic floor-cleaning device in a hospital or laboratory environment.

2. Background of the Invention

Autonomous robot cleaning devices are known in the art. For example, U.S. Pat. Nos. 5,940,927 and 5,781,960 disclose an Autonomous Surface Cleaning Apparatus and a Nozzle Arrangement for a Self-Guiding Vacuum Cleaner. Also, U.S. Pat. Nos. 6,605,156 and 6,883,201 disclose improved, automated cleaning devices with self-contained power supplies. Particularly, these devices provide optimized cleaning efficiency under reduced power requirements. Nonetheless, these devices are not adapted to provide cleaning of surfaces using sterile, disposable cleaning assemblies. In other words, after said cleaning devices clean a dirty floor, the incorporated brushes and surfaces in contact with said floor become contaminated. As such, their use in environments where the transfer of pathogens cannot be allowed to occur, such as a hospital operating room, is obviated. Therefore, an invention that allows a robotic floor-cleaning device to repeatedly clean a sensitive environment while maintaining sanitary and sterile conditions would be of benefit.

SUMMARY AND OBJECTS OF THE INVENTION

An automated (robotic) floor-cleaner, such as the commercially available SCOOBA® or FLOOR GENIE™, is adapted to allow sterile cleaning of sensitive environments, such as a hospital operating room. In particular, the floor-cleaner chassis is redesigned to be mounted on a deck containing cleaning devices that contact the floor. The cleaning devices mounted on the deck, which can comprise such cleaning devices as vacuum heads, brushes, cleaning fluid sprays, and conceivably sanitizing devices such as a UV germicidal light, are provided pre-sterilized. As such, the adapted floor-cleaner chassis allows the deck to be mounted to the bottom of the chassis; the floor cleaner is then used to clean a floor, after which, the deck is removed from the chassis and disposed. The robotic-floor cleaner and sterilization system cleans floors between or even during cases. The system's disposable, sterile cleaning-cassettes ensure a sterile environment. Further, the robotic floor cleaner reduces the "turnover time" required between cases, as it operates simultaneously while staff prepare the room for the next case.

The present invention comprises a housing infrastructure including
- a chassis,
- a power subsystem for providing the energy to power the autonomous floor-cleaning robot,
- a motive subsystem operative to propel and operate the autonomous floor-cleaning robot for cleaning operations,
- a control module, such as an on-board computer, operative to control the autonomous floor-cleaning robot to effect cleaning operations, and
- a cleaning subsystem that includes
  - a sterile, disposable deck which latches into and mounts in pivotal combination with the chassis,
  - a brush assembly mounted in deck and powered by the motive subsystem to sweep up particulates during cleaning operations,
  - a vacuum assembly disposed in combination with the deck and powered by the motive subsystem to ingest particulates during cleaning operations, and
  - a spray assembly disposed in combination with the deck and powered by the motive subsystem to disperse fluids, such as cleaning fluid, during cleaning operations.

Therefore, one object of the present invention is to provide a sterile cleaning device that is operable without human intervention to clean designated areas.

It is another object of the present invention to provide an automated floor-cleaning device adapted to receive a sterile, disposable cartridge attachable to the lower chassis of said floor-cleaning device.

It is yet another object of the present invention to provide a sterile, disposable cartridge for use with automated floor-cleaning devices.

At least one of the above objects is met in whole or in part by the present invention. Additional objects are apparent by the following description and claims.

BRIEF DESCRIPTION OF THE DRAWINGS

The present invention can best be understood in connection with the accompanying drawings. It is noted that the invention is not limited to the precise embodiments shown in drawings, in which.

BRIEF DESCRIPTION OF REFERENCE NUMERALS

100 Robotic Floor Cleaner with Cartridge; 102 Sterile, Disposable Cartridge; 104 Light; 106 On/Off Switch; 108

Rechargeable Battery; 110 Cover; 112 Waste Receptacle; 114 Vacuum; 116 Motor/Impeller; 118 Bumper; 120 Brush; 120' Brush; 122 Reusable Chassis; 124 Independent Motors; 126 Cleaning Fluid Reservoir; 128 Spray Nozzle; 130 Floor; 132 Vacuum Inlet; 134 Wheel; 136 Castor; 138 Side Handles with Latch Bar Control; 138' Counter-Latch; 141 Motor; 142 Latching Slots; 144 Brush Motor Drive Socket; 146 Drive Motor Shaft Socket; 148 Vacuum Connections; 150 Water/Cleaning Fluid Connection

DETAILED DESCRIPTION OF THE INVENTION

Figure 1:
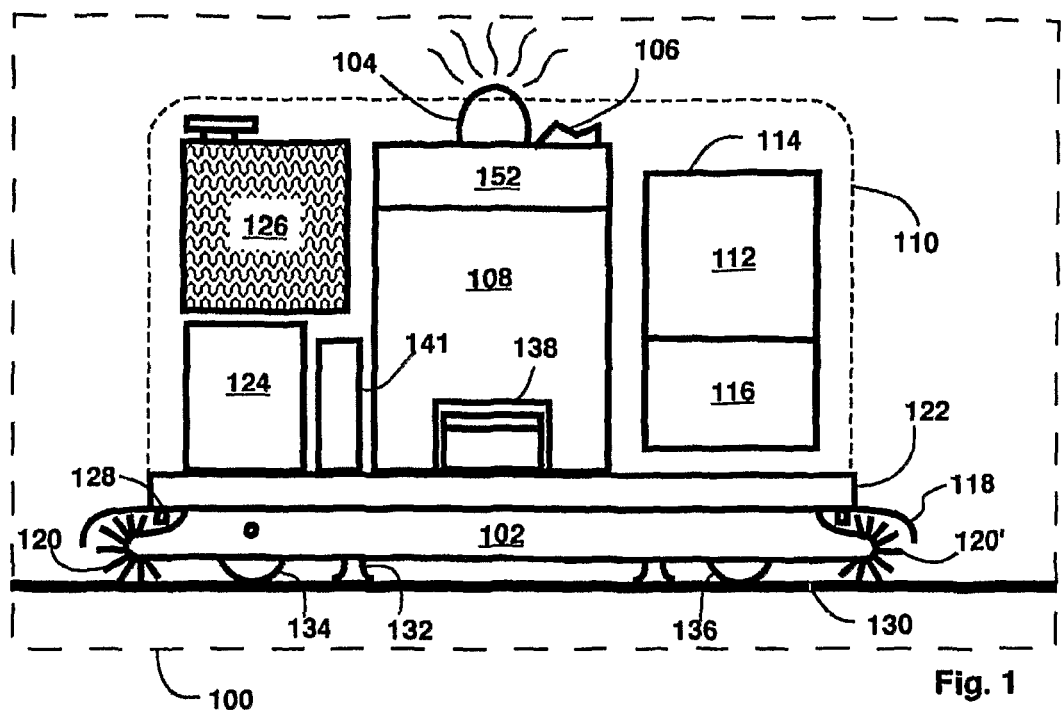
FIG. 1 is a side elevation view in partial cutaway of a robotic floor cleaner in accordance with the invention.
Figure 2:
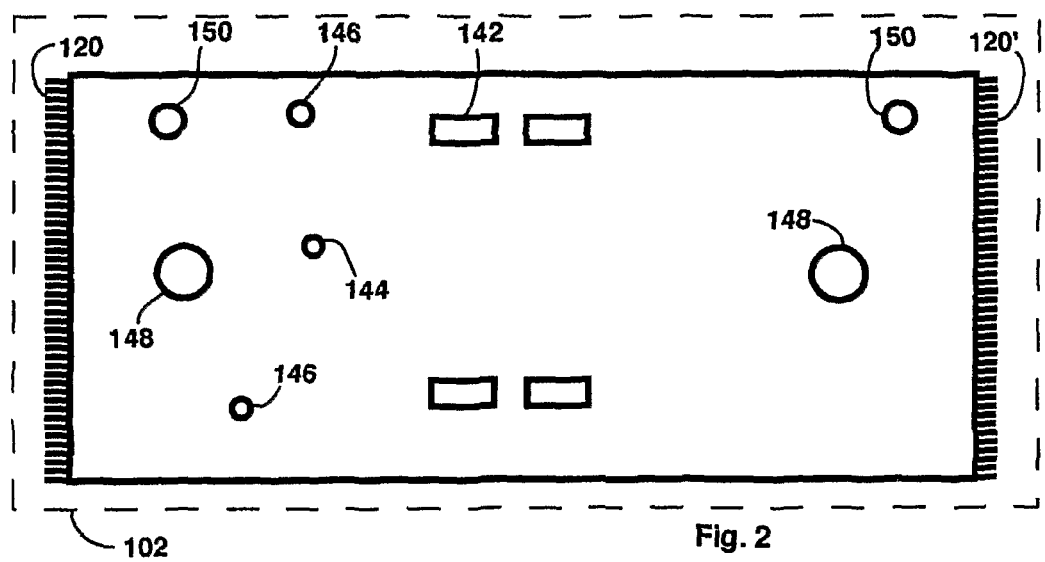
FIG. 2 is a top plan view of the disposable portion of the robotic floor cleaner depicted in FIG. 1.

FIGS. 1 and 2 show a modified robotic floor cleaner, such as a modified FLOOR GENIE™, I-ROBOT® SCOOBA, or I-ROBOT® ROOMBA. The floor cleaner incorporates sterile disposable elements. FIG. 1 shows a Robotic Floor Cleaner with Cartridge 100 with cover 110 shown in a cutaway view to reveal its interior, and to show the placement of some of the major components. Reference numeral 122 is the chassis of the reusable portion of the Robotic Floor Cleaner with Cartridge 100. Portion 102 below is a disposable unit that is re-supplied in a sterile pack, with connections to reusable chassis portion 122. An optional bumper 118 may be provided around the Robotic Floor Cleaner with Cartridge 100. Disposable Portion 102 of the Robotic Floor Cleaner with Cartridge 100 has wet scrubbing brushes 120' at the front and brushes 120 at the rear. These are connected to, and driven by, motor 141 within the non-disposable, reusable portion 122. Cleaning fluid in reservoir 126 is sprayed through nozzles 128, which have back-flow preventers to prevent reverse contamination of fluid supply reservoir 126. Vacuum cleaner 114 is also provided with motor/impeller 116, and receptacle 112 has vacuum inlets 132 at the front and back of disposable portion 102.

The entire Robotic Floor Cleaner with Cartridge 100 is powered by rechargeable battery pack 108 and is controlled by computer 152. Flashing light 104 indicates operation and ON/OFF switch 106 is preferably provided at a top of reusable portion 122. The drive configuration is similar to that of a zero turning radius riding lawnmower. Here, the two fixed drive wheels 134 are driven by two independent motors 124 near the front. Two passive swiveling casters 136 are near the rear. Side handles 138 with latch bar control coupling and de-coupling from disposable platform 102 that carries both drive wheels 134, brushes 120 and 120' as well as casters 136.

FIG. 2 is a top plan view of disposable platform 102 of Robotic Floor Cleaner with Cartridge 100 showing alignment and latching slots 142 that engage with the top reusable portion 122. Vacuum connections 148 and water/cleaning fluid connections 150 are illustrated as well as drive motor shaft sockets 146 and brush motor drive socket 144. Although autonomous and very maneuverable, the accuracy and/or simplicity of the guidance system can be enhanced with waypoint emitters, embedded in the floor surface, that are detectable by computer 152 via appropriate sensors.

Figure 3:
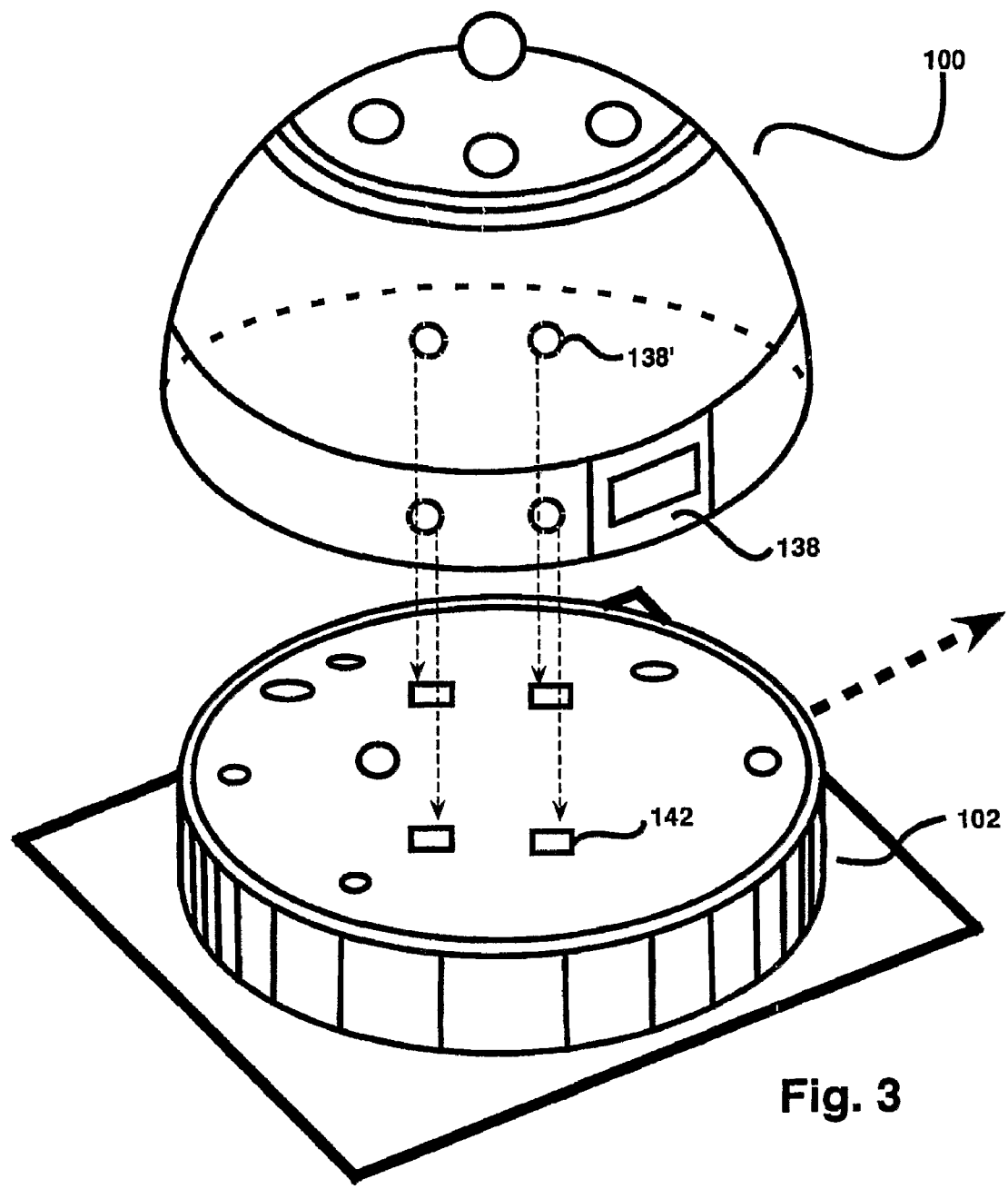
FIG. 3 is a perspective view of the top chassis being inserted onto the deck.

FIG. 3 shows a perspective view. As can be seen by the figure, any one embodiment of the invention can have various shapes. In this example, the deck and upper portion of the device is rounded. The large dotted arrow indicates a direction of movement for the cleaning device. The top reusable portion 122 is being inserted into latches 142 guided into place by side handles and latch bar control 138. The handles 138 can also function to disengage counter-latch 138' from latches 142, thereby allowing removal of the deck and top reusable portion.

In the foregoing description, certain terms and visual depictions are used to illustrate the preferred embodiment. However, no unnecessary limitations are to be construed by the terms used or illustrations depicted, beyond what is shown in the prior art, since the terms and illustrations are exemplary only, and are not meant to limit the scope of the present invention. It is further known that other modifications may be made to the present invention, without departing the scope of the invention, as noted in the appended claims.

I claim:

1. A robotic floor cleaner for locations needing sterile conditions, comprising:
   a chassis;
   a rechargeable battery connected to a top portion of the chassis for providing energy to power said floor-cleaner;
   at least one motor connected to the top portion of the chassis for providing energy to propel and operate said robotic floor cleaner for cleaning operations; and
   a disposable cleaning portion removably attached to a bottom portion of the chassis, the disposable cleaning portion comprising a brush assembly, a vacuum assembly and a spray assembly and provided in a sterile pack.

2. An automated floor cleaning device comprising:
   a reusable portion comprising a chassis supporting a drive motor, a vacuum motor having an impeller and vacuum connections, a cleaning fluid reservoir having cleaning fluid connections, a rechargeable battery, a receptacle, a computer and a cover, wherein the chassis further comprises a lower portion having at least one latch; and
   a pre-sterilized disposable cartridge removably attached to the reusable portion, wherein the pre-sterilized disposable cartridge comprises vacuum inlets operably connected to the vacuum motor connections, nozzles operably connected to the cleaning fluid connections, wet scrubbing brushes, and brushes;
   wherein the pre-sterilized disposable cartridge further comprises alignment and latching slots for removable attachment to the at least one latch of the chassis.

3. The device of claim 2, wherein the nozzles comprise backflow preventers configured to prevent reverse contamination of fluid in the fluid reservoir.

4. The device of claim 2, further comprising a second disposable cartridge in a sterile pack.

5. The device of claim 2, further comprising:
   two fixed drive wheels connected near a front portion of the chassis and operably connected to the drive motor; and
   two passive swiveling wheels operably connected to a rear portion of the chassis.

6. The device of claim 5, wherein each of the two fixed drive wheels is operably connected to an independent drive motor.

7. The device of claim 2, further comprising at least one sensor connected to the chassis and operably connected to the computer, the at least one sensor configured to detect at least one way point emitter embedded in a floor.

8. A method comprising:
   attaching a cleaning deck to a bottom portion of a floor cleaner chassis to form a robotic floor cleaner and cleaning deck apparatus, wherein the cleaning deck comprises a plurality of pre-sterilized cleaning devices;
   cleaning a floor with the robotic floor cleaner and cleaning deck apparatus;
   removing the cleaning deck after the floor has been cleaned; and
   disposing of the cleaning deck.

9. The method of claim 8, further comprising attaching another cleaning deck comprising a plurality of pre-sterilized cleaning devices to the bottom portion of the chassis.

10. The method of claim 8, wherein the plurality of pre-sterilized cleaning devices comprises at least two of vacuum heads, wet brushes, brushes, cleaning fluid nozzles and a sanitizing device.

11. The method of claim 10, wherein the sanitizing device comprises a UV germicidal light.

12. The method of claim 10, wherein the cleaning fluid nozzles comprise backflow preventers configured to prevent reverse contamination.

* * * * *